(12) United States Patent
Cole et al.

(10) Patent No.: US 11,134,446 B2
(45) Date of Patent: Sep. 28, 2021

(54) SYSTEMS, DEVICES, AND METHODS FOR POWER-EFFICIENT WIRELESS COMMUNICATIONS BETWEEN ELECTRONIC DEVICES

(71) Applicant: ABBOTT DIABETES CARE INC., Alameda, CA (US)

(72) Inventors: Jean-Pierre Cole, Tracy, CA (US); Xuandong Hua, Mountain View, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 16/265,545

(22) Filed: Feb. 1, 2019

(65) Prior Publication Data

US 2019/0246357 A1      Aug. 8, 2019

Related U.S. Application Data

(60) Provisional application No. 62/626,611, filed on Feb. 5, 2018.

(51) Int. Cl.
*H04W 52/02* (2009.01)
*A61B 5/145* (2006.01)
*H04W 48/10* (2009.01)
*H04W 8/00* (2009.01)

(52) U.S. Cl.
CPC ..... *H04W 52/0251* (2013.01); *A61B 5/14532* (2013.01); *H04W 8/005* (2013.01); *H04W 48/10* (2013.01)

(58) Field of Classification Search
CPC .... H04W 52/025; H04W 48/10; H04W 8/005
See application file for complete search history.

(56) References Cited

U.S. PATENT DOCUMENTS

| | | |
|---|---|---|
| 2005/0059383 A1* | 3/2005 | Williamson ........... G06Q 30/02 455/414.1 |
| 2006/0233146 A1 | 10/2006 | Nagata et al. |
| 2008/0009692 A1 | 1/2008 | Stafford |
| 2011/0213225 A1 | 9/2011 | Bernstein et al. |
| 2011/0319729 A1 | 12/2011 | Donnay et al. |
| 2015/0018639 A1 | 1/2015 | Stafford |
| 2015/0025345 A1 | 1/2015 | Funderburk et al. |

(Continued)

OTHER PUBLICATIONS

WO, PCT/US2019/016297 ISR and Written Opinion, dated May 20, 2019.

(Continued)

*Primary Examiner* — Jamal Javaid
(74) *Attorney, Agent, or Firm* — One LLP

(57) ABSTRACT

Systems, devices and methods are provided for power-efficient wireless communications between electronic devices. In particular, the embodiments disclosed herein can reduce battery consumption in a transmitting electronic device and enhance data integrity of data received by a receiving electronic device. According to the embodiments, a first electronic device transmits advertising packets according to a wireless communications protocol, wherein the advertising packets include a first payload data. In response to receiving the advertising packets, a second electronic device can transmit a scan request to the first electronic device which, in turn, terminates the transmission of advertising packets.

20 Claims, 11 Drawing Sheets

(56) References Cited

U.S. PATENT DOCUMENTS

| | | |
|---|---|---|
| 2015/0173661 A1 | 6/2015 | Myles |
| 2015/0289207 A1 | 10/2015 | Kubo et al. |
| 2017/0026777 A1* | 1/2017 | Denboer ............... H04W 8/005 |
| 2017/0325161 A1* | 11/2017 | Kwon .................... H04W 76/10 |
| 2018/0027412 A1* | 1/2018 | Mandapaka .......... H04W 74/04 |
| | | 713/151 |
| 2018/0152829 A1* | 5/2018 | Fujiwara ............... H04W 84/18 |
| 2018/0360314 A1 | 12/2018 | Wang et al. |

OTHER PUBLICATIONS

Bluetooth Low Energy Technology Training, All Hands Meeting, Apr. 19-22, 2010.

Specification of the Bluetooth System, vol. 0—Master Table of Contents & Compliance Requirements, Covered Core Package version: 4.0, Jun. 30, 2010.

Specification of the Bluetooth System, vol. 1—Architecture & Terminology Overview, Covered Core Package version: 4.0, Jun. 30, 2010.

Specification of the Bluetooth System, vol. 2—Core System Package [BR/EDR Controller volume], Covered Core Package version: 4.0, Jun. 30, 2010.

Specification of the Bluetooth System, vol. 3—Core System Package [Host volume], Covered Core Package version: 4.0, Jun. 30, 2010.

Specification of the Bluetooth System, vol. 4—Host Controller Interface [Transport Layer], Covered Core Package version: 4.0, Jun. 30, 2010.

Specification of the Bluetooth System, vol. 5—Core System Package [AMP Controller volume], Covered Core Package version: 4.0, Jun. 30, 2010.

Specification of the Bluetooth System, vol. 6—Core System Package [Low Energy Controller volume], Covered Core Package version: 4.0, Jun. 30, 2010.

* cited by examiner

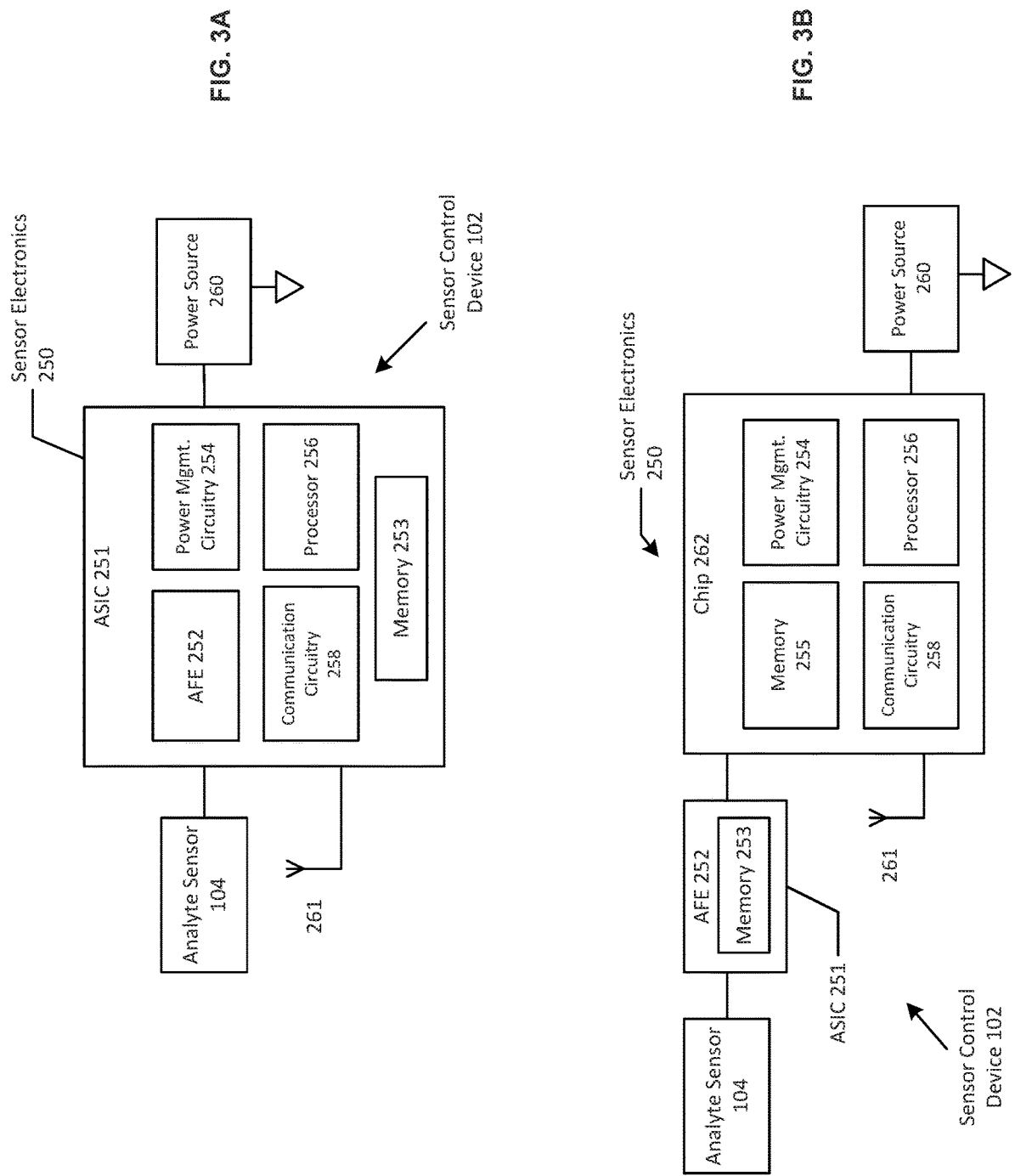

SYSTEMS, DEVICES, AND METHODS FOR POWER-EFFICIENT WIRELESS COMMUNICATIONS BETWEEN ELECTRONIC DEVICES

CROSS-REFERENCE TO RELATED APPLICATIONS

This application claims the benefit of and priority to U.S. Provisional Patent Application Ser. No. 62/626,611, filed Feb. 5, 2018, which is incorporated by reference herein in its entirety and for all purposes.

FIELD

The subject matter described herein relates generally to systems, devices, and methods for power-efficient wireless communications between electronic devices. In particular, the embodiments disclosed herein relate to the use of advertising schemes for the wireless transmission of data between electronic devices, which may include a low-powered sensor device and a receiver.

BACKGROUND

The prevalence of wireless connectivity between electronic devices has steadily increased over the years. As Internet-enabled devices, such as Internet-of-Things ("IoT") devices, have become ubiquitous, so to have the components that enable these devices to wirelessly communicate with each other. To keep up with the growing number of applications for wireless connectivity and communications, manufacturers of wireless communications components, such as Bluetooth radios, have sought to add more on-chip resources to their products. As a result, many commercially available wireless communications components have become complex systems on chip ("SOC"), providing numerous interfaces such as analog-to-digital converters, references, operational amplifiers, and the like.

For certain applications, however, the rising complexity of wireless communications components have led to significant challenges in power efficiency and/or data integrity. For example, with respect to electronic devices having limited power, the inclusion of unneeded functions can result in unwanted and unnecessary power consumption. To illustrate, one example from the medical arts is an in vivo analyte monitoring system, in which a sensor control device (or other on body device) is worn on the body of an individual to monitor an analyte level in the body. The sensor control device may be configured to wirelessly transmit sensor data to another device, from which the individual or her health care provider can review the individual's data and make therapy decisions. The sensor control device may also have a small form-factor, to increase comfort and convenience to the individual, and can include a battery that is not easily replaced or recharged. In this example, it is important for the sensor control unit to be as power efficient as possible, so that the individual can continue to monitor her health. Similar challenges can arise in non-medical applications, such as with electronic devices in the aerospace, marine or nanotechnology fields, where wireless communications between electronic devices having limited power are needed.

For these and other reasons, needs exist for methods, systems and devices for power-efficient wireless communications between electronic devices.

SUMMARY

Provided herein are example embodiments of systems, devices and methods for power-efficient wireless communications between electronic devices. According to one aspect of the embodiments, a first electronic device transmits a first plurality of advertising or advertisement packets according to a wireless communications protocol, where the advertising packets can include a first payload data. In many of the embodiments disclosed herein, the wireless communications protocol can be a Bluetooth or Bluetooth Low Energy ("BLE") protocol. According to another aspect of the embodiments, a second electronic device receives the first plurality of advertising packets and, in response, transmits a scan request packet to the first electronic device. The first electronic device receives the scan request and, in response, terminates the transmission of the first plurality of advertising packets.

In some embodiments, the first electronic device, in response to receiving the scan request, can identify a second plurality of advertising packets that was not previously received by the second electronic device, and subsequently transmit a scan response packet to the second electronic device. The scan response packet can include a second payload data associated with the second plurality of advertising packets that was not previously received by the second electronic device.

The embodiments disclosed herein have application in both medical and non-medical fields. As one example, the embodiments can be implemented in an analyte monitoring system, including a sensor control device (or other on body device) configured to be worn on an individual's body, where the sensor control unit includes one or more processors, non-transitory memory, wireless communications circuitry, and an analyte sensor configured to sense an analyte level in a bodily fluid of the individual. The sensor control device can have a small form-factor for the individual's comfort and convenience. In addition, the sensor control device can communicate with a reader device (or "reader") according to a wireless communication protocol, such as by a Bluetooth Low Energy protocol. In particular, instructions stored in the memory of the sensor control unit, when executed by the one or more processors, can cause the one or more processors to cause a transmission of advertising packets to the reader device, where the advertising packets can include data indicative of a sensed analyte level. Furthermore, the transmission of the advertising packets can be terminated upon the sensor control device receiving a scan request from the reader device.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 3A and 3B are block diagrams depicting example embodiments of sensor control devices.

DETAILED DESCRIPTION

Figure 1A:
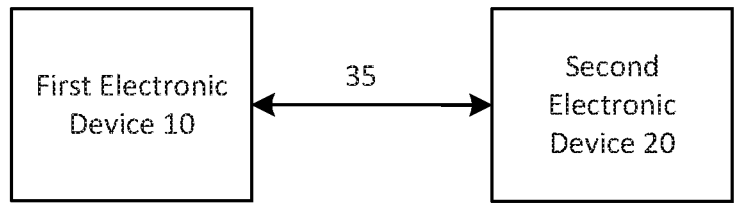
FIGS. 1A-1C are block diagrams depicting various wireless communications schemes between electronic devices.

Before the present subject matter is described in detail, it is to be understood that this disclosure is not limited to the particular embodiments described herein, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure are used with systems, devices, and methods for power-efficient wireless communications between electronic devices. Accordingly, many embodiments include at least one electronic device that can have a compact form-factor and include a limited power supply, such as a battery. For example, some of the embodiments may be utilized with in vivo analyte monitoring systems for detecting at least one analyte, such as glucose, in a bodily fluid (e.g., subcutaneously within the interstitial fluid ("ISF") or blood, within the dermal fluid of the dermal layer, or otherwise). Accordingly, many embodiments include in vivo analyte sensors structurally configured so that at least a portion of the sensor is, or can be, positioned in the body of a user to obtain information about at least one analyte of the body. However, the embodiments disclosed herein can be used in either medical or non-medical applications that incorporate electronic devices having limited power.

Furthermore, for each and every embodiment of a method disclosed herein, systems and devices capable of performing each of those embodiments are covered within the scope of the present disclosure. For example, embodiments of electronic devices, sensor control devices, reader devices, and components thereof are disclosed, and these devices and components can have one or more antenna for wireless communications, non-transitory memories (e.g., for storing instructions and data), power sources, wireless communication circuits, transmitters, receivers, processors and/or controllers (e.g., for executing instructions stored in memory) that can perform any and all method steps, or facilitate the execution of any and all method steps.

As mentioned, electronic devices having limited power can often have a compact size or relatively small form factor, and this may lead to problems or disadvantages relating to cost and power optimization, among other issues. For example, one trend among component manufacturers has been to include as many on-chip resources as possible to address a wide variety of applications. As a result, wireless components have become rather complex systems on chip ("SOC"), providing various interfaces such as analog-to-digital converters, references, operational amplifiers, and the like. However, certain applications, such as sensing applications, often do not require all the functionality and interfaces provided in these multi-purpose catalog SOCs. Rather, sensing applications may only need to be able to transmit data occasionally or periodically at very low rates for use by one or more receivers. Thus, these multi-purpose catalog SOCs utilized for wireless communications can be costly and include unnecessary functions.

One approach that has been proposed for wireless communications in electronic devices with limited power is to utilize a transmit-only wireless architecture, in which the electronic device includes only the transmit portion of a radio for transmitting data at a rate sufficient to ensure that a receiver can receive data as intended. However, due to a lack of acknowledgement from the receiver, and to ensure completeness of data, a transmit-only system would need to transmit at a rate and duration likely greater than necessary. This would result in a waste of precious battery capacity, which is highly undesirable in small form-factor devices where changing or recharging a battery is infeasible.

These embodiments and others described herein represent technological improvements in the field of wireless electronic devices. As described in further detail below, the embodiments disclosed herein can include, for example, a first electronic device utilizing a Bluetooth Low Energy advertising scheme, in which a first payload data can be transmitted to a second electronic device. In response, a scan request can be transmitted from the second electronic device to the first electronic device, that serves to (1) acknowledge that a complete set of payload data has been received, and (2) cause the first electronic device to terminate the transmission of advertising packets and thus conserve battery life. In this regard, the disclosed embodiments reflect an improvement in power efficiency. As another advantage, to overcome certain limitations associated with mobile operating systems, some of the embodiments disclosed herein can also utilize a scan response, transmitted from the first electronic device to the second electronic device, to backfill any missing payload data on the second electronic device.

Thus, the embodiments also reflect an improvement in accuracy and device interoperability. Other improvements and advantages of the disclosed embodiments are described below, and will be apparent to those of skill in the art.

Example Embodiments of Power-Efficient Wireless Communications Schemes

Provided herein are embodiments of power-efficient wireless communications schemes for use between electronic devices having limited power. Many of the embodiments described herein can have application in the medical arts, as described further below. Those of skill in the art, however, will recognize that these embodiments can have application in non-medical fields, such as aerospace, marine, and nanotechnology fields, or any field of art in which wireless communications are desired between electronic devices, where at least one of the electronic devices has a limited power supply or a power supply that cannot be easily recharged or replaced.

Figure 1B:
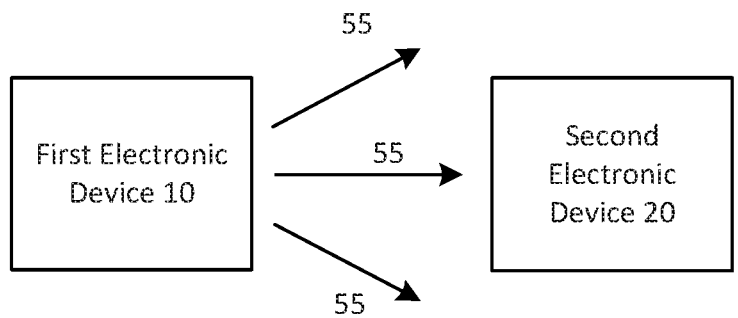
Figure 1C:
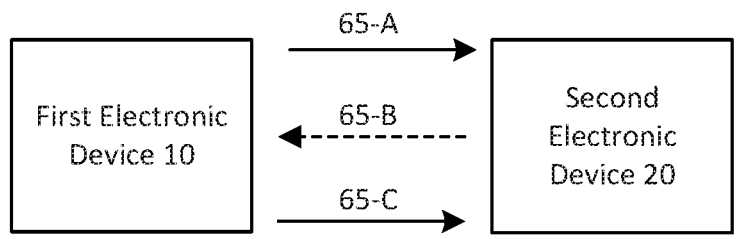

FIGS. 1A-1C are block diagrams depicting various wireless communications schemes between electronic devices. It will be understood by those of skill in the art that the electronic devices shown in these Figures can each include, at least, one or more processors, memory coupled to the one or more processors, wireless communications circuitry, and a power supply. Furthermore, for any of the processes, methods, or method steps described below, those of skill in the art will understand that each of the steps included in the processes, methods, or method steps can be stored as instructions in the respective memories of the electronic devices, and that the instructions, when executed by the one or more respective processors of the electronic devices, can cause the one or more respective processors to perform any of the processes, methods, or methods steps described herein. It will also be apparent to those of skill in the art that the wireless communications schemes described herein can be performed according to a standard wireless protocol, such as a Bluetooth or Bluetooth Low Energy protocol, or a proprietary wireless protocol that is capable of unidirectional wireless transmissions, such as advertising, broadcasting, multicasting, and the like.

FIG. 1A is a block diagram depicting wireless communications scheme 25 between multiple electronic devices, including first electronic device 10 and second electronic device 20. As shown in FIG. 1A, first electronic device 10 is capable of wirelessly communicating with second electronic device 20 via wireless communications link 35. In this case, wireless communications link 35 is a bi-directional connection established between the first and second electronic devices 10, 20. First electronic device 10 is configured to both transmit and receive data through wireless communications link 35, and can include a multi-function transceiver, such as a multi-function SoC wireless communications component. As described earlier, problems of power efficiency can arise in wireless communications scheme 25 particularly where first electronic device 10 has a limited power supply, and where the numerous functions of the multi-function SoC wireless communications component are not being utilized.

FIG. 1B is a block diagram depicting another wireless communications scheme 50 between first electronic device 10 and second electronic device 20. In this case, wireless communications scheme 50 depicts a transmit-only wireless architecture. As shown in FIG. 1B, first electronic device 10 includes only a transmit portion (e.g., transmitter without a receiver) in its wireless communications circuitry, and transmits data through wireless communications link 55. Since no acknowledgement can be received from second electronic device 20, first electronic device 10 will repeatedly transmit data through wireless communications link 55 for a period of time sufficient to ensure that the data has been received by second electronic device 20. As described earlier, problems of power efficiency can also arise in wireless communications scheme 50 because first electronic device 10 may continue to transmit even after second electronic device 20 has received the data.

FIG. 1C is a block diagram depicting an example embodiment of wireless communications scheme 75 between first electronic device 10 and second electronic device 20. According to one aspect of the embodiment, first electronic device 10 can transmit data using advertising packets, as denoted by wireless communications link 65-A. In response to receiving advertising packets, second electronic device 20 can return a scan request through wireless communications link 65-B, as denoted with a dashed line. Upon receiving the scan request, first electronic device 10 can terminate the transmission of advertising packets to second electronic device 20, and thus conserve power. Furthermore, in some embodiments, as shown in FIG. 1C, first electronic device 10 can also identify, based on received scan requests, if second electronic device 20 has not received any of the previously transmitted advertising packets. In response to identifying "missing" advertising packets, first electronic device 10 can transmit a scan response containing the missing data to second electronic device 20 over wireless communications link 65-C, to enhance integrity of the data on second electronic device 20.

Figure 1D:
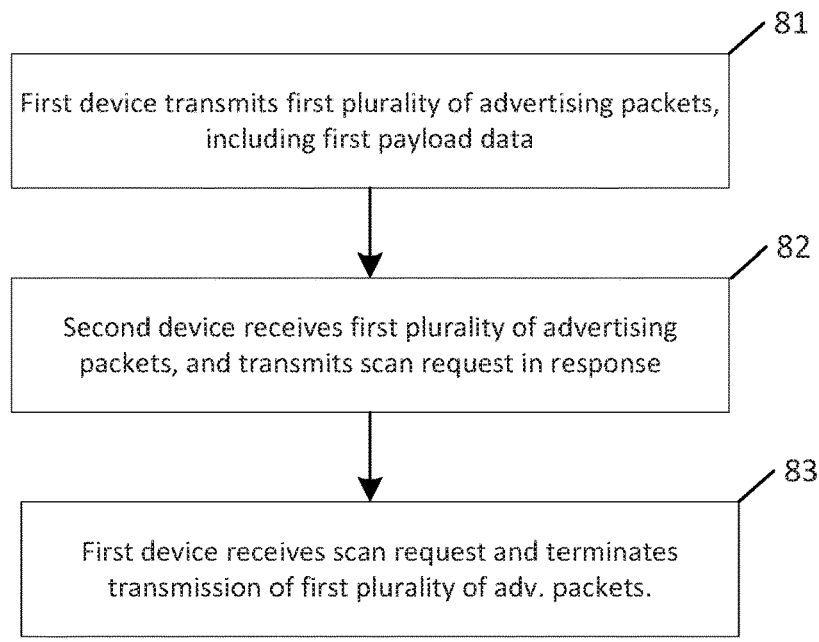
FIG. 1D-1F are flow charts of example embodiments of methods for power-efficient wireless communications between electronic devices.
Figure 1E:
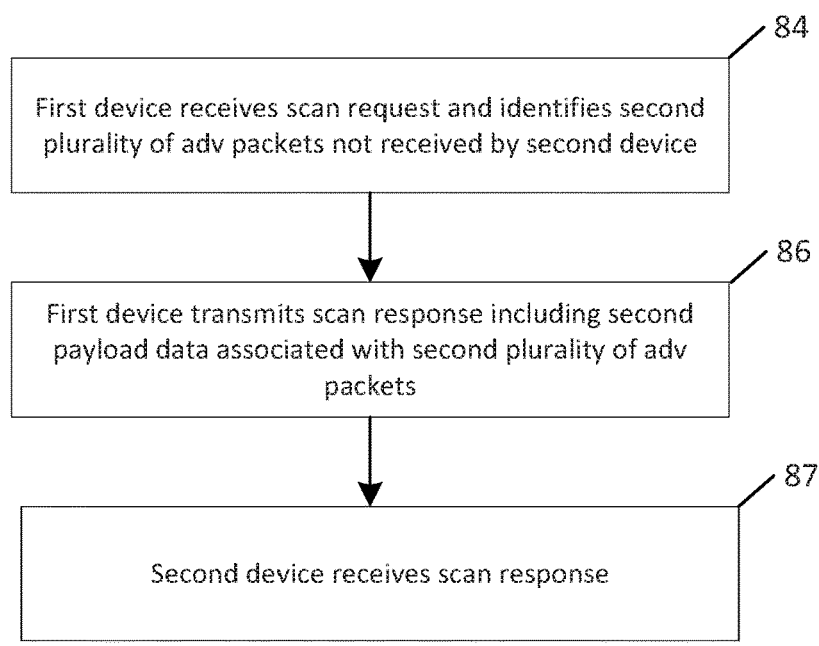
Figure 1F:
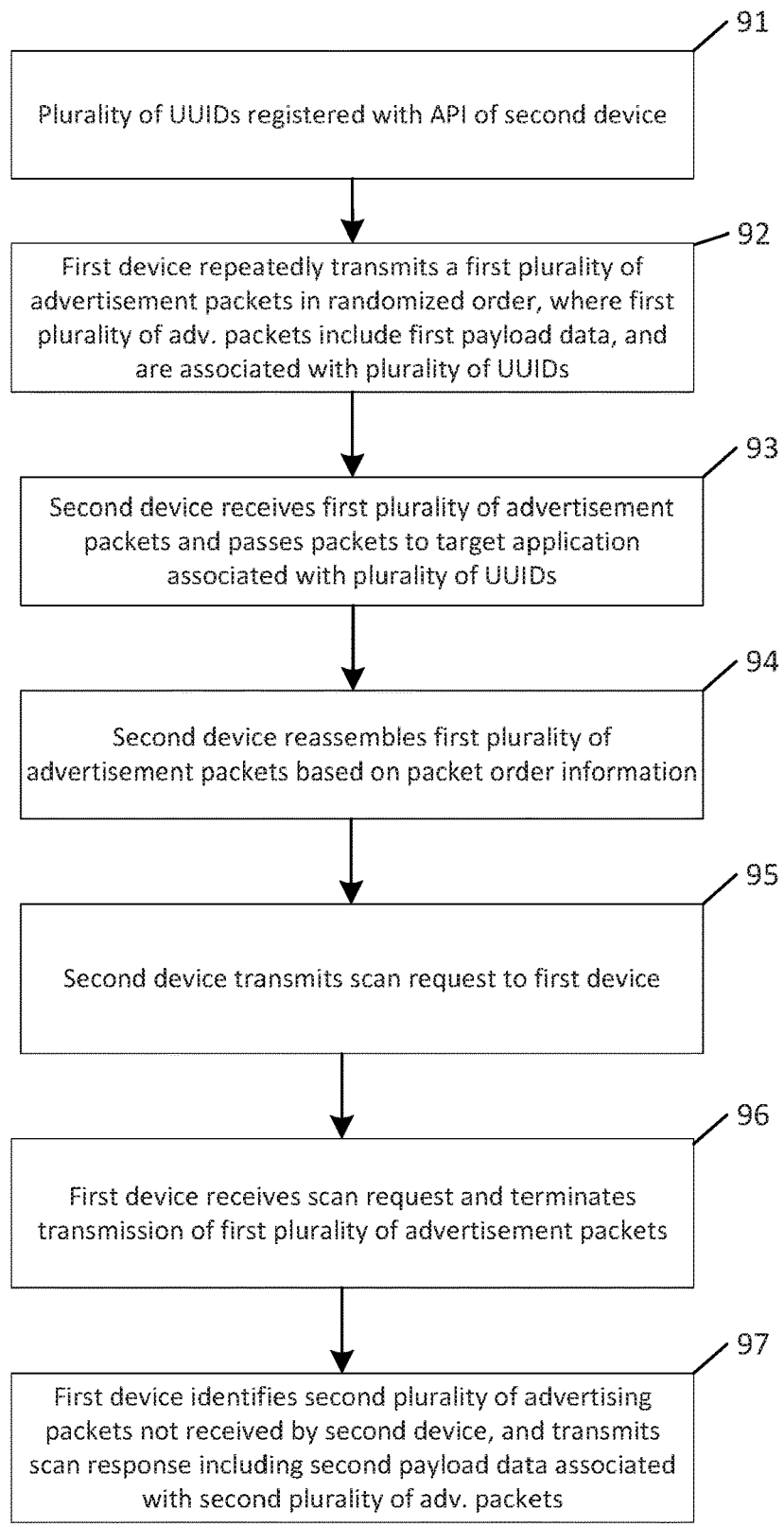

FIGS. 1D-1F are flow diagrams depicting example embodiments of various methods for power-efficient wireless communications between electronic devices, the steps of which relate to the embodiment previously described with respect to wireless communications scheme 75. Turning to FIG. 1D, a flow diagram is provided for a method 80 for power-efficient wireless communications between electronic devices. At Step 81, first device 10 transmits a first plurality of advertising packets according to a wireless communications protocol, where the first plurality of advertising packets includes payload data. In some embodiments, for example, where first device 10 is a sensor device, payload data can include information indicative of a sensed measurement (e.g., temperature, pressure, force, acceleration, physiological parameter, etc.). At Step 82, the first plurality of advertising packets is received by a second device 20. In some embodiments, second device 20 can be a reader device configured to visually output the sensed measurement to a display, such as a smart phone, tablet or wearable computing device. In other embodiments, second device 20 can be a personal computer, laptop, workstation, server or any other computing device configured to wirelessly receive data. In response to receiving the first plurality of advertising packets, second device 20 transmits a scan request packet to first device 10. At Step 83, in response to receiving the scan request from second device 20, first device 10 can terminate the transmission of the first plurality of advertising packets, and thereby conserve power.

FIG. 1E is a flow diagram depicting a "data backfilling" feature of an example embodiment of a method 85 for power-efficient wireless communications between electronic devices. At Step 84, first device 10 receives a scan request from second device 20, and subsequently identifies a second plurality of advertising packets that was not received by second device 20. According to one aspect of the embodiments, each scan request transmitted by second device 20 can be associated with a plurality of advertising packets received by second device 20. First device 10 can then track the received scan requests from second device 20, and thus can determine if second device 20 has not previously received certain advertising packets based on any missing received scan requests. If it is determined, for example, that second device 20 has not received a second plurality of advertising packets, at Step 86, first device 10 can then transmit a scan response to second device 20, where the scan response includes payload data associated with the "missing" second plurality of advertising packets. At Step 87, second device 20 receives the scan response that includes the payload data. In this regard, method 85 can enhance data integrity on second device 20.

FIG. 1F is a flow diagram depicting an example embodiment of a method 90 for power-efficient wireless communications between electronic devices, where the second electronic device is a mobile computing device that includes a mobile operating system (e.g., Apple iOS, Android, etc.). At Step 91, a plurality of Universal Unique Identifiers (UUIDs) are registered with an Application Program Interface (API) of second device 20. At Step 92, first device 10 repeatedly transmits a first plurality of advertising packets in a randomized order, where the first plurality of advertising packets includes a first payload data, and where each of the packets of the first plurality of advertising packets is associated with the plurality of UUIDs. At Step 93, second device 20 receives the first plurality of advertising packets and, based on the UUIDs associated with the packets, passes the packets to a target application associated with the UUIDs. At Step 94, second device 20 reassembles the advertising packets based on packet order information that is stored in each of the first plurality of advertising packets. At Step 95, second device 20 then transmits a scan request packet to first device 10. At Step 96, first device 10 receives the scan request and terminates transmission of the first plurality of advertising packets, thereby conserving power. In some embodiments, at Step 97, first device 10 can also identify a second plurality of advertising packets not received by second device 20, and transmit a scan response to second device 20, where the scan response includes a second payload data associated with the "missing" second plurality of advertising packets. In this regard, the integrity of the data on second device 20 is enhanced.

Example Embodiments of Analyte Monitoring Systems

As mentioned earlier, the embodiments disclosed herein can be used in either medical or non-medical applications that incorporate electronic devices having limited power. To illustrate the implementation of these embodiments in a particular field, an example medical field is described, particularly that of analyte monitoring. While this description helps elaborate and illustrate the details of the embodiments, it is merely an example of one of the many fields in which the embodiments can be implemented, including medical fields other than analyte monitoring, and non-medical fields including (but not limited to) those other fields described herein. Thus, to the extent these embodiments are described with respect to devices intended for use in analyte monitoring, it is intended that these embodiments are likewise applicable to generic electronic devices, or those that are for use in other fields.

Before describing these aspects of the embodiments in detail, however, it is first desirable to describe examples of devices that can be present within a system for use in analyte monitoring, such as, for example, a sensor control device that transmits data measured with an in vivo analyte sensor, as well as examples of these devices' operation, all of which can be used with the embodiments described herein.

There are various types of analyte monitoring systems. "Continuous Analyte Monitoring" systems (or "Continuous Glucose Monitoring" systems), for example, are in vivo systems that can transmit data from a sensor control device to a reader device repeatedly or continuously without prompting, e.g., automatically according to a schedule. "Flash Analyte Monitoring" systems (or "Flash Glucose Monitoring" systems or simply "Flash" systems), as another example, are in vivo systems that can transfer data from a sensor control device in response to a request for data by a reader device, such as with a Near Field Communication (NFC) or Radio Frequency Identification (RFID) protocol. In vivo analyte monitoring systems can also operate without the need for finger stick calibration.

In vivo monitoring systems can include a sensor that, while positioned in vivo, makes contact with the bodily fluid of the user and senses one or more analyte levels contained therein. The sensor can be part of a sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few. As used herein, these terms are not limited to devices with analyte sensors, and encompass devices that have sensors of other types, whether biometric or non-biometric. The term "on body" refers to any device that resides directly on the body or in close proximity to the body, such as a wearable device (e.g., glasses, watch, wristband or bracelet, neckband or necklace, etc.).

In vivo monitoring systems can also include one or more reader devices that receive sensed analyte data from the sensor control device. These reader devices can process and/or display the sensed analyte data, in any number of forms, to the user. These devices, and variations thereof, can be referred to as "handheld reader devices," "reader devices" (or simply, "readers"), "handheld electronics" (or handhelds), "portable data processing" devices or units, "data receivers," "receiver" devices or units (or simply receivers), "relay" devices or units, or "remote" devices or units, to name a few. Other devices such as personal computers have also been utilized with or incorporated into in vivo and in vitro monitoring systems.

In vivo analyte monitoring systems can be differentiated from "in vitro" systems that contact a biological sample outside of the body (or rather "ex vivo") and that typically include a meter device that has a port for receiving an analyte test strip carrying bodily fluid of the user, which can be analyzed to determine the user's blood sugar level.

In vivo analyte monitoring systems can be differentiated from "in vitro" systems that contact a biological sample outside of the body (or rather "ex vivo") and that typically include a meter device that has a port for receiving an analyte test strip carrying a bodily fluid of the user, which can be analyzed to determine the user's analyte level. As mentioned, the embodiments described herein can be used with in vivo systems, in vitro systems, and combinations thereof.

Figure 2A:
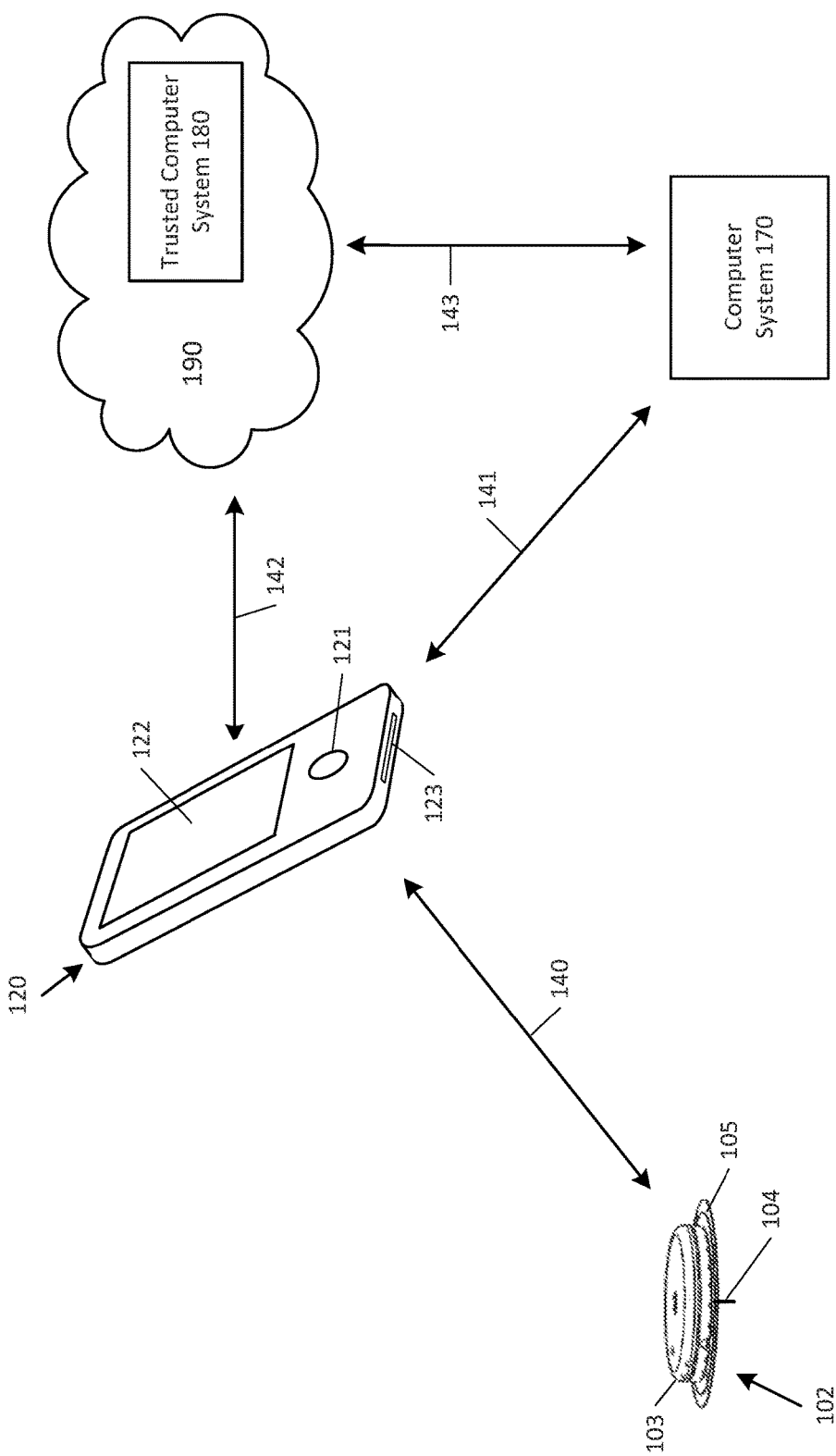
FIG. 2A is a system overview of a sensor control device, reader, network, local computer system and trusted computer system.

The embodiments described herein can be used to monitor and/or process information regarding any number of one or more different analytes. Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times FIG. 2A is a conceptual diagram depicting an example embodiment of an in vivo analyte monitoring system 100 that includes a sensor control device 102 and a reader device 120. Sensor control device 102 (which is further described with respect to FIGS. 3A and 3B) can be applied to a monitoring location on a user's skin such that a sensor 104 is maintained in position in the user's body for a period of time by an adhesive patch 105. In addition, sensor control device 102 and reader 120 can communicate with each over a local communication path (or link) 140. In embodiments where path 140 is wireless, a wireless communication protocol such as Bluetooth or Bluetooth Low Energy (BLE, BTLE, Bluetooth SMART, Bluetooth SMART Ready, etc.) can be used. Bluetooth is a well-known standardized short range wireless communication protocol, and Bluetooth Low Energy is a version of the same that requires less power to operate. A version of BTLE is described in the Bluetooth Specification, version 4.0, published Jun. 30, 2010. In other embodiments, other wireless communications protocols can be used, such as Wi-Fi, a proprietary protocol, or any other wireless communication protocol in existence as of the date of this filing or their later developed variants.

Reader device 120 is also capable of wired, wireless, or combined communication with a computer system 170 (e.g., a local or remote computer system) over communication path (or link) 141 and with a network 190, such as the internet or the cloud, over communication path (or link) 142. Communication with network 190 can involve communication with trusted computer system 180 within network 190, or though network 190 to computer system 170 via communication link (or path) 143. Communication paths 141, 142, and 143 can be wireless, wired, or both, can be uni-directional or bi-directional, and can be part of a telecommunications network, such as a Wi-Fi network, a local area network (LAN), a wide area network (WAN), the internet, or other data network. In some cases, communication paths 141 and 142 can be the same path. All communications over paths 140, 141, and 142 can be encrypted, and sensor control device 102, reader device 120, computer system 170, and trusted computer system 180 can each be configured to encrypt and decrypt those communications sent and received.

Variants of devices 102 and 120, as well as other components of an in vivo-based analyte monitoring system that are suitable for use with the system, device, and method embodiments set forth herein, are described in US Patent Application Publ. No. 2011/0213225 (the '225 Publication), which is incorporated by reference herein in its entirety for all purposes.

Referring still to FIG. 2A, sensor control device 102 can include a housing 103 containing in vivo analyte monitoring circuitry and a power source. In this embodiment, the in vivo analyte monitoring circuitry is electrically coupled with an analyte sensor 104 that extends through an adhesive patch 105 and projects away from housing 103. Adhesive patch 105 contains an adhesive layer (not shown) for attachment to a skin surface of the body of the user. Other forms of body attachment to the body may be used, in addition to or instead of adhesive.

Sensor 104 is adapted to be at least partially inserted into the body of the user, where it can make fluid contact with that user's bodily fluid (e.g., subcutaneous (subdermal) fluid, dermal fluid, or blood) and be used, along with the in vivo analyte monitoring circuitry, to measure analyte-related data of the user. Sensor 104 and any accompanying sensor control electronics can be applied to the body in any desired manner. For example, an insertion device (not shown) can be used to position all or a portion of analyte sensor 104 through an external surface of the user's skin and into contact with the user's bodily fluid. In doing so, the insertion device can also position sensor control device 102 with adhesive patch 105 onto the skin. In other embodiments, insertion device can position sensor 104 first, and then accompanying sensor control electronics can be coupled with sensor 104 afterwards, either manually or with the aid of a mechanical device. Examples of insertion devices are described in U.S. Publication Nos. 2008/0009692, 2011/0319729, 2015/0018639, 2015/0025345, and 2015/0173661, all which are incorporated by reference herein in their entireties and for all purposes.

After collecting raw data from the user's body, sensor control device 102 can apply analog signal conditioning to the data and convert the data into a digital form of the conditioned raw data. In some embodiments, this conditioned raw digital data can be encoded for transmission to another device, e.g., reader device 120, which then algorithmically processes that digital raw data into a final form representative of the user's measured biometric (e.g., a form readily made suitable for display to the user). This algorithmically processed data can then be formatted or graphically processed for digital display to the user. In other embodiments, sensor control device 102 can algorithmically process the digital raw data into the final form that is representative of the user's measured biometric (e.g., analyte level) and then encode and wirelessly communicate that data to reader device 120, which in turn can format or graphically process the received data for digital display to the user. In other embodiments, sensor control device 102 can graphically process the final form of the data such that it is ready for display, and display that data on a display of sensor control device 102 or transmit the data to reader device 120. In some embodiments, the final form of the biometric data (prior to graphic processing) is used by the system (e.g., incorporated into a diabetes monitoring regime) without processing for display to the user. In some embodiments, sensor control device 102 and reader device 120 can transmit the digital raw data to another computer system for algorithmic processing and display.

Reader device 120 can include a display 122 to output information to the user and/or to accept an input from the user, and an optional input component 121 (or more), such as a button, actuator, touch sensitive switch, capacitive switch, pressure sensitive switch, jog wheel or the like, to input data, commands, or otherwise control the operation of reader device 120. In certain embodiments, display 122 and input component 121 may be integrated into a single component, for example, where the display can detect the presence and location of a physical contact touch upon the display, such as with a touch screen user interface. In certain embodiments, input component 121 of reader device 120 may include a microphone and reader device 120 may include software configured to analyze audio input received from the microphone, such that functions and operation of the reader device 120 may be controlled by voice commands. In certain embodiments, an output component of reader device 120 includes a speaker (not shown) for outputting information as audible signals. Similar voice responsive components such as a speaker, microphone and software routines to generate, process and store voice driven signals may be included in sensor control device 102.

Reader device 120 can also include one or more data communication ports 123 for wired data communication with external devices such as computer system 170 or sensor control device 102. Example data communication ports include USB ports, mini USB ports, USB Type-C ports, USB micro-A and/or micro-B ports, RS-232 ports, Ethernet ports, Firewire ports, or other similar data communication ports configured to connect to the compatible data cables. Reader device 120 may also include an integrated or attachable in vitro glucose meter, including an in vitro test strip port (not shown) to receive an in vitro glucose test strip for performing in vitro blood glucose measurements.

Reader device 120 can display the measured biometric data wirelessly received from sensor control device 102 and can also be configured to output alarms, alert notifications, glucose values, etc., which may be visual, audible, tactile, or any combination thereof. Further details and other display embodiments can be found in, e.g., U.S. Publication 2011/0193704, which is incorporated herein by reference in its entirety for all purposes.

Reader device 120 can function as a data conduit to transfer the measured data from sensor control device 102 to computer system 170 or trusted computer system 180. In certain embodiments, the data received from sensor control device 102 may be stored (permanently or temporarily) in one or more memories of reader device 120 prior to uploading to system 170, 180 or network 190.

Computer system 170 may be a personal computer, a server terminal, a laptop computer, a tablet, or other suitable data processing device. Computer system 170 can be (or include) software for data management and analysis and communication with the components in analyte monitoring system 100. Computer system 170 can be used by the user or a medical professional to display and/or analyze the biometric data measured by sensor control device 102. In some embodiments, sensor control device 102 can communicate the biometric data directly to computer system 170 without an intermediary such as reader device 120, or indirectly using an internet connection (also, optionally, without first sending the data to reader device 120). Operation and use of computer system 170 is further described in the '225 Publication incorporated herein. Analyte monitoring system 100 can also be configured to operate with a data processing module (not shown), also as described in the incorporated '225 Publication.

Trusted computer system 180 can be within the possession of the manufacturer or distributor of sensor control device 102, either physically or virtually through a secured connection, and can be used to perform authentication of sensor control device 102, for secure storage of the user's biometric data, and/or as a server that serves a data analytics program (e.g., accessible via a web browser) for performing analysis on the user's measured data.

Example Embodiments of Reader Devices

Reader device 120 can be a mobile communication device such as a dedicated reader device (configured for communication with a sensor control device 102, and optionally a computer system 170, but without mobile telephony communication capability), or a mobile telephone including, but not limited to, a Wi-Fi or internet-enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as Google glasses, which is a mobile communication device). This optical assembly can have a transparent display that displays information about the user's analyte level (as described herein) to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 2B:
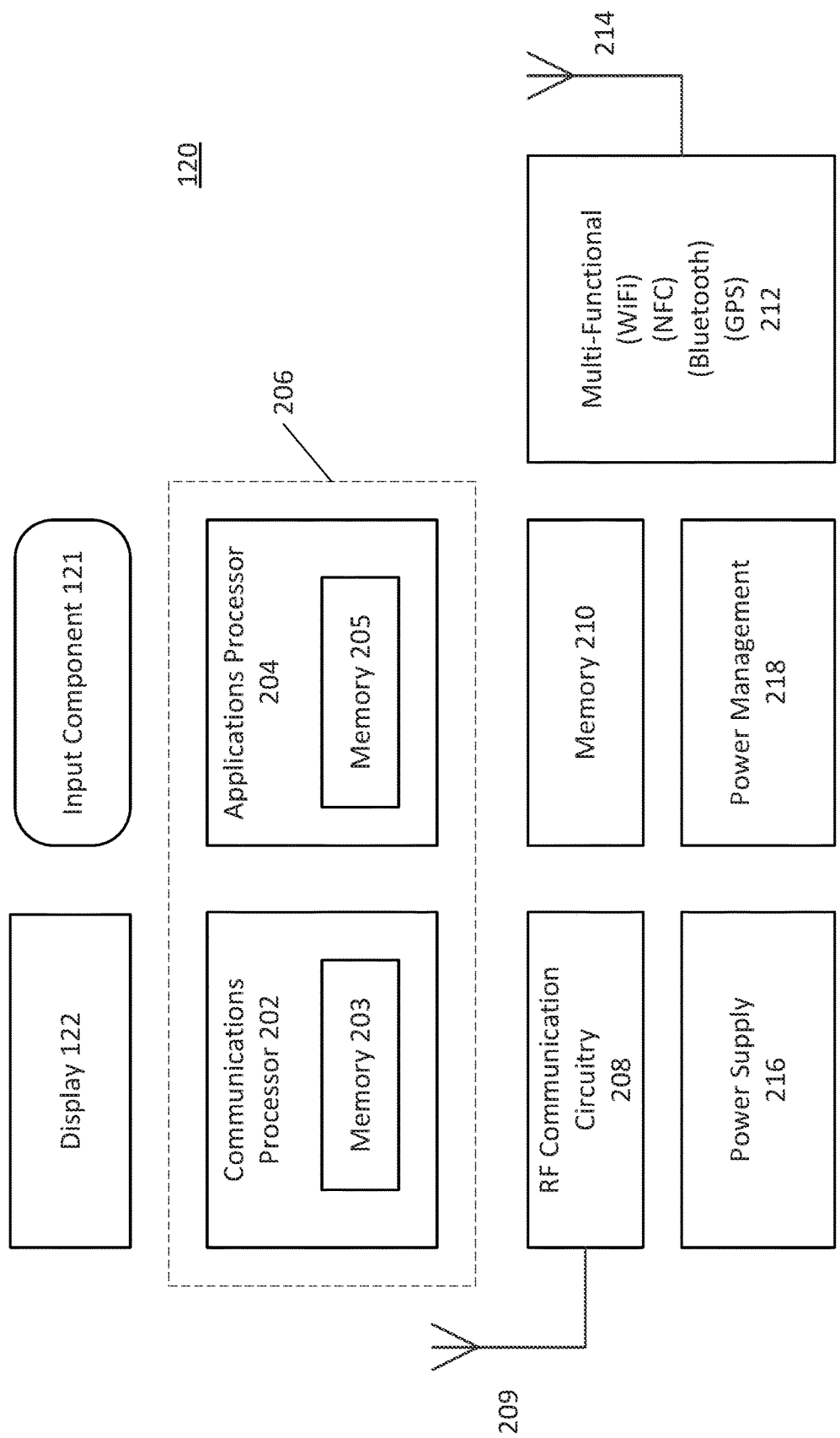
FIG. 2B is a block diagram depicting an example embodiment of a reader.

FIG. 2B is a block diagram of an example embodiment of a reader device 120 configured as a smart phone. Here, reader device 120 includes an input component 121, display 122, and processing circuitry 206, which can include one or more processors, microprocessors, controllers, and/or microcontrollers, each of which can be a discrete chip or distributed amongst (and a portion of) a number of different chips. Here, processing circuitry 206 includes a communications processor 202 having on-board memory 203 and an applications processor 204 having on-board memory 205. Reader device 120 further includes RF communication circuitry 208 coupled with an RF antenna 209, a memory 210, multi-functional circuitry 212 with one or more associated antennas 214, a power supply 216, and power management circuitry 218. FIG. 2 is an abbreviated representation of the typical hardware and functionality that resides within a smart phone and those of ordinary skill in the art will readily recognize that other hardware and functionality (e.g., codecs, drivers, glue logic) can also be included.

Communications processor 202 can interface with RF communication circuitry 208 and perform analog-to-digital conversions, encoding and decoding, digital signal processing and other functions that facilitate the conversion of voice, video, and data signals into a format (e.g., in-phase and quadrature) suitable for provision to RF communication circuitry 208, which can then transmit the signals wirelessly. Communications processor 202 can also interface with RF communication circuitry 208 to perform the reverse functions necessary to receive a wireless transmission and convert it into digital data, voice, and video. RF communication circuitry 208 can include a transmitter and a receiver (e.g., integrated as a transceiver) and associated encoder logic.

Applications processor 204 can be adapted to execute the operating system and any software applications that reside on reader device 120, process video and graphics, and perform those other functions not related to the processing of communications transmitted and received over RF antenna 209. The smart phone operating system will operate in conjunction with a number of applications on reader device 120. Any number of applications (also known as "user interface applications") can be running on reader device 120 at any one time, and may include one or more applications that are related to a diabetes monitoring regime, in addition to the other commonly used applications that are unrelated to such a regime, e.g., email, calendar, weather, sports, games, etc. For example, the data indicative of a sensed analyte level and in vitro blood analyte measurements received by the reader device can be securely communicated to user interface applications residing in memory 210 of reader device 120. Such communications can be securely performed, for example, through the use of mobile application containerization or wrapping technologies.

Memory 210 can be shared by one or more of the various functional units present within reader device 120, or can be distributed amongst two or more of them (e.g., as separate memories present within different chips). Memory 210 can also be a separate chip of its own. Memories 203, 205, and 210 are non-transitory, and can be volatile (e.g., RAM, etc.) and/or non-volatile memory (e.g., ROM, flash memory, F-RAM, etc.).

Multi-functional circuitry 212 can be implemented as one or more chips and/or components (e.g., transmitter, receiver, transceiver, and/or other communication circuitry) that perform other functions such as local wireless communications, e.g., with sensor control device 102 under the appropriate protocol (e.g., Bluetooth, Bluetooth Low Energy, Wi-Fi, proprietary protocols, and others) and determining the geographic position of reader device 120 (e.g., global positioning system (GPS) hardware). One or more other antennas 214 are associated with the functional circuitry 212 as needed to operate with the various protocols and circuits.

Power supply 216 can include one or more batteries, which can be rechargeable or single-use disposable batteries. Power management circuitry 218 can regulate battery charging and power supply monitoring, boost power, perform DC conversions, and the like.

Reader device 120 can also include or be integrated with a drug (e.g., insulin, etc.) delivery device such that they, e.g., share a common housing. Examples of such drug delivery devices can include medication pumps having a cannula that remains in the body to allow infusion over a multi-hour or multi-day period (e.g., wearable pumps for the delivery of basal and bolus insulin). Reader device 120, when combined with a medication pump, can include a reservoir to store the drug, a pump connectable to transfer tubing, and an infusion cannula. The pump can force the drug from the reservoir, through the tubing and into the diabetic's body by way of the cannula inserted therein. Other examples of drug delivery devices that can be included with (or integrated with) reader device 120 include portable injection devices that pierce the skin only for each delivery and are subsequently removed (e.g., insulin pens). A reader device 120, when combined with a portable injection device, can include an injection needle, a cartridge for carrying the drug, an interface for controlling the amount of drug to be delivered, and an actuator to cause injection to occur. The device can be used repeatedly until the drug is exhausted, at which point the combined device can be discarded, or the cartridge can be replaced with a new one, at which point the combined device can be reused repeatedly. The needle can be replaced after each injection.

The combined device can function as part of a closed-loop system (e.g., an artificial pancreas system requiring no user intervention to operate) or semi-closed loop system (e.g., an insulin loop system requiring seldom user intervention to operate, such as to confirm changes in dose). For example, a diabetic's analyte level can be monitored in a repeated automatic fashion by sensor control device 102, which can then communicate that monitored analyte level to reader device 120, and the appropriate drug dosage to control the diabetic's analyte level can be automatically determined and subsequently delivered to the diabetic's body. Software instructions for controlling the pump and the amount of insulin delivered can be stored in the memory of reader device 120 and executed by the reader device's processing circuitry. These instructions can also cause calculation of drug delivery amounts and durations (e.g., a bolus infusion and/or a basal infusion profile) based on the analyte level measurements obtained directly or indirectly from sensor control device 102. In some embodiments sensor control device 102 can determine the drug dosage and communicate that to reader device 120.

Example Embodiments of Sensor Control Devices

FIGS. 3A and 3B are block diagrams depicting example embodiments of sensor control devices 102 each including an analyte sensor 104 and sensor electronics 250 (including analyte monitoring circuitry) that, collectively, can have the majority of the processing capability for rendering end-result data, such as analyte metrics, which are suitable for display to the user. In FIG. 3A, a single semiconductor chip 251 is depicted that can be a custom application specific integrated circuit (ASIC). Shown within ASIC 251 are certain high-level functional units, including an analog front end (AFE) 252, power management (or control) circuitry 254, processor 256, and communication circuitry 258 (which can be implemented as a transmitter, receiver, transceiver, passive circuit, or otherwise according to the communication protocol). In this embodiment, both AFE 252 and processor 256 are used as in vivo analyte monitoring circuitry, but in other embodiments either circuit can perform the monitoring functions. Processor 256 can include one or more processors, microprocessors, controllers, and/or microcontrollers, each of which can be a discrete chip or distributed amongst (and a portion of) a number of different chips.

A non-transitory memory 253 is also included within ASIC 251 and can be shared by the various functional units present within ASIC 251, or can be distributed amongst two or more of them. Memory 253 can also be a separate chip. Memory 253 can be volatile and/or non-volatile memory. In this embodiment, ASIC 251 is coupled with power source 260, which can be a coin cell battery, or the like. AFE 252 interfaces with in vivo analyte sensor 104 and receives measurement data therefrom and outputs the data to processor 256 in digital form. Processor 256, in turn, can execute one or more instructions stored in memory 253, which can cause processor 256 to process the data. This data can then be provided to communication circuitry 258 for sending, by way of antenna 261, to reader device 120 (not shown), for example, where minimal further processing is needed by the resident software application to display the data. Antenna 261 can be configured according to the needs of the application and communication protocol. Antenna 261 can be, for example, a printed circuit board (PCB) trace antenna, a ceramic antenna, or a discrete metallic antenna. Antenna 261 can be configured as a monopole antenna, a dipole antenna, an F-type antenna, a loop antenna, and others.

Information may be communicated from sensor control device 102 to a second device (e.g., reader device 120) at the initiative of sensor control device 102 or reader device 120. For example, information can be transmitted repeatedly (e.g., continuously) by sensor control device 102 when the analyte information is available, or according to a schedule (e.g., about every 1 minute, about every 5 minutes, about every 10 minutes, or the like), in which case the information can be stored or logged in a memory of sensor control device 102 for later communication. The information can be transmitted from sensor control device 102 in response to receipt of a request by the second device. This request can be an automated request, e.g., a request transmitted by the second device according to a schedule, or can be a request generated at the initiative of a user (e.g., an ad hoc or manual request). In some embodiments, the second device can transmit a polling signal or data packet to sensor control device 102, and device 102 can treat each poll (or polls occurring at certain time intervals) as a request for data and, if data is available, then can transmit such data to the second device. In many embodiments, the communication between sensor control device 102 and the second device are secure (e.g., encrypted and/or between authenticated devices), but in some embodiments the data can be transmitted from sensor control device 102 in an unsecured manner, e.g., as a broadcast to all listening devices in range.

Different types and/or forms and/or amounts of information may be sent as part of each communication including, but not limited to, one or more of current sensor measurements (e.g., the most recently obtained analyte level information temporally corresponding to the time the reading is initiated), rate of change of the measured metric over a predetermined time period, rate of the rate of change of the metric (acceleration in the rate of change), or historical metric information corresponding to metric information obtained prior to a given reading and stored in a memory of sensor control device 102. In some embodiments, sensor control device 102 collects raw measurement data from the body and transmits that raw data (with or without signal conditioning, and with or without other data such as temperature data) to reader device 120 for further algorithmic processing into a format representative of the wearer's analyte levels, which can then be displayed (or made displayable) by reader device 120. In other embodiments, that algorithmic processing is performed by sensor control device 102 prior to transmission to reader device 120.

Some or all of real time, historical, rate of change, rate of rate of change (such as acceleration or deceleration) information may be sent to reader device 120 in a given communication or transmission. In certain embodiments, the type and/or form and/or amount of information sent to reader device 120 may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments reader device 120 can output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of sensor control device 102 (e.g., in the form of a graphical trace). Additionally, an on-skin or sensor temperature reading or measurement may be communicated from sensor control device 102 with each data communication. The temperature reading or measurement, however, may be used in conjunction with a software routine executed by reader device 120 to correct or compensate the analyte measurement output to the user, instead of or in addition to actually displaying the temperature measurement to the user.

FIG. 3B is similar to FIG. 3A, but instead depicts two discrete semiconductor chips 252 and 262, which can be packaged together or separately. Here, AFE 252 is resident on ASIC 251. As shown here, AFE 252 is coupled to analyte sensor 104. Referring to chip 262, processor 256 is integrated with power management circuitry 254 and communication circuitry 258 on chip 262. AFE 252 includes memory 253 and chip 262 includes memory 255, which can be isolated or distributed within. In one example embodiment (not shown), AFE 252 is combined with power management circuitry 254 and processor 256 on one chip, while communication circuitry 258 is on a separate chip. In another example embodiment (also not shown), both AFE 252 and communication circuitry 258 are on one chip, and processor 256 and power management circuitry 254 are on another chip. It should be noted that other chip combinations are possible, including three or more chips, each bearing responsibility for the separate functions described, or sharing one or more functions for fail-safe redundancy.

Example Embodiments of Wireless Communication Schemes in Analyte Monitoring Systems Wireless communications in analyte monitoring systems, such as those between a sensor control device and a reader, can present various challenges with respect to cost, power efficiency and economy, data reliability, and device interoperability. For example, in analyte monitoring systems having a sensor control unit with a compact form-factor, power-efficient wireless communication schemes are desirable, especially where the sensor control device may have a small battery that cannot be easily replaced or recharged. In this regard, many wireless communication components on the market today are not optimized for use in analyte monitoring systems because, as described earlier, certain components, such as multi-function catalog SOCs, can include various unneeded functions that not only raise the cost of the component, but can also diminish the battery capacity in the sensor control device. Utilizing a simple transmit-only wireless architecture, e.g., having only the transmit portion of a radio, can also create issues of power efficiency and economy because, without the capability to receive an acknowledgement of receipt from a reader, the sensor control device transmits sensor data at a higher rate to ensure that the reader has successfully received the sensor data as intended. In this regard, a transmit-only architecture can also result in diminished battery capacity.

In addition to power efficiency, device interoperability and data integrity are also important considerations in selecting a wireless communication scheme for an analyte monitoring system. For example, in analyte monitoring systems where the reader is a smart phone, certain limitations of the smart phone's operating system may cause the smart phone to be unable to receive a complete set of sensor data. In particular, applications on a smart phone are generally required to register a Universal Unique Identifier (UUID) of the primary service with a Bluetooth Low Energy (BLE) Application Program Interface (API) in order for the smart phone to receive advertising packets according to a BLE protocol, so that the smart phone scans for advertising packets and can pass the data to the application when the packets are received. To conserve the phone battery, however, some smart phone operating systems scan for the advertising packets infrequently, which makes the sensor data delivery through the advertising packets challenging. In addition to consuming the sensor device's battery power, sometimes the delivery of the sensor data cannot be achieved at all because there may be a sending window time constraint in the sensor design. In addition, after the smart phone has received an advertising packet and has passed the information to the smart phone's application, it will filter out advertising packets of the same UUID. When sensor data is sent in multiple BLE advertising packets due to the limited size of each packet, only part of the sensor data may be delivered to the phone application.

Provided herein are embodiments of power-efficient wireless communication schemes for use in an analyte monitoring system that can reduce battery consumption in the sensor control device and enhance data integrity of the sensor data received by the reader. These embodiments can implement these schemes using a BLE or normal Bluetooth protocol, or other protocol. These embodiments can communicate and transfer analyte-related data collected by the sensor using a relatively simple link layer protocol that enables the reader to scan the sensor control device. For example, the sensor control device can transmit analyte data using a BLE or Bluetooth transmission such as one or more advertising packets. In the example of BLE, scanning provides a way for the reader to acknowledge receipt of the analyte data in the advertising packet and/or request additional data from the sensor control device, e.g., with a scan request Protocol Data Unit (PDU) or other format provided in the BLE, Bluetooth, or other respective protocol. The sensor control device can interpret the receipt of a scan request as an acknowledgement from the receiver that it received the transmitted advertising packet. With this acknowledgement, the sensor can terminate advertising, avoiding the wasted power of continuing to transmit data that has already been received by the reader. Based on the scan request PDU, the sensor control device can determine whether data was not received or stored by the reader and retransmit that data using, e.g., a scan response PDU or other format provided in the BLE, Bluetooth, or other respective protocol.

Most of the complexity in BLE or Bluetooth comes with the formation of a formal pairing between devices. These embodiments permit the sensor control device and reader to communicate analyte data and maintain data integrity without establishing such a BLE or Bluetooth pairing. This allows further power savings, and allows one or both devices to omit the more powerful and robust microcontroller and memory necessary to establish and maintain such pairings, which can result in further cost savings.

As described with respect to FIGS. 3A and 3B, sensor control device 102 can include one or more processors 256, a memory 255 coupled to the one or more processors, wireless communications circuitry 258 coupled to the one or more processors 256, and an analyte sensor 104 configured to sense an analyte level in a bodily fluid of a subject. According to one aspect of the embodiments, memory 255 of sensor control device 102 can store instructions that, when executed by the one or more processors 256, cause the one or more processors 256 to cause the transmission of advertising packets according to a wireless communications protocol, where one or more of the advertising packets include data indicative of the sensed analyte level. Each packet transmission can be repeated continuously with little or no time interval therebetween, or each packet can be transmitted at a regular interval (e.g., 5 seconds, 10 seconds, 30 seconds, one minute, two minutes, five minutes, ten minutes, and so forth), or packets can be sent in rapid or near-rapid sequence with a regular interval between one sequence and the next. According to another aspect of the embodiments, memory 255 of sensor control device 102 can store further instructions that, when executed by the one or more processors 256, cause the one or more processors 256 to terminate the transmission of the advertising packets in response to the receiving a scan request from reader 120.

Figure 4:
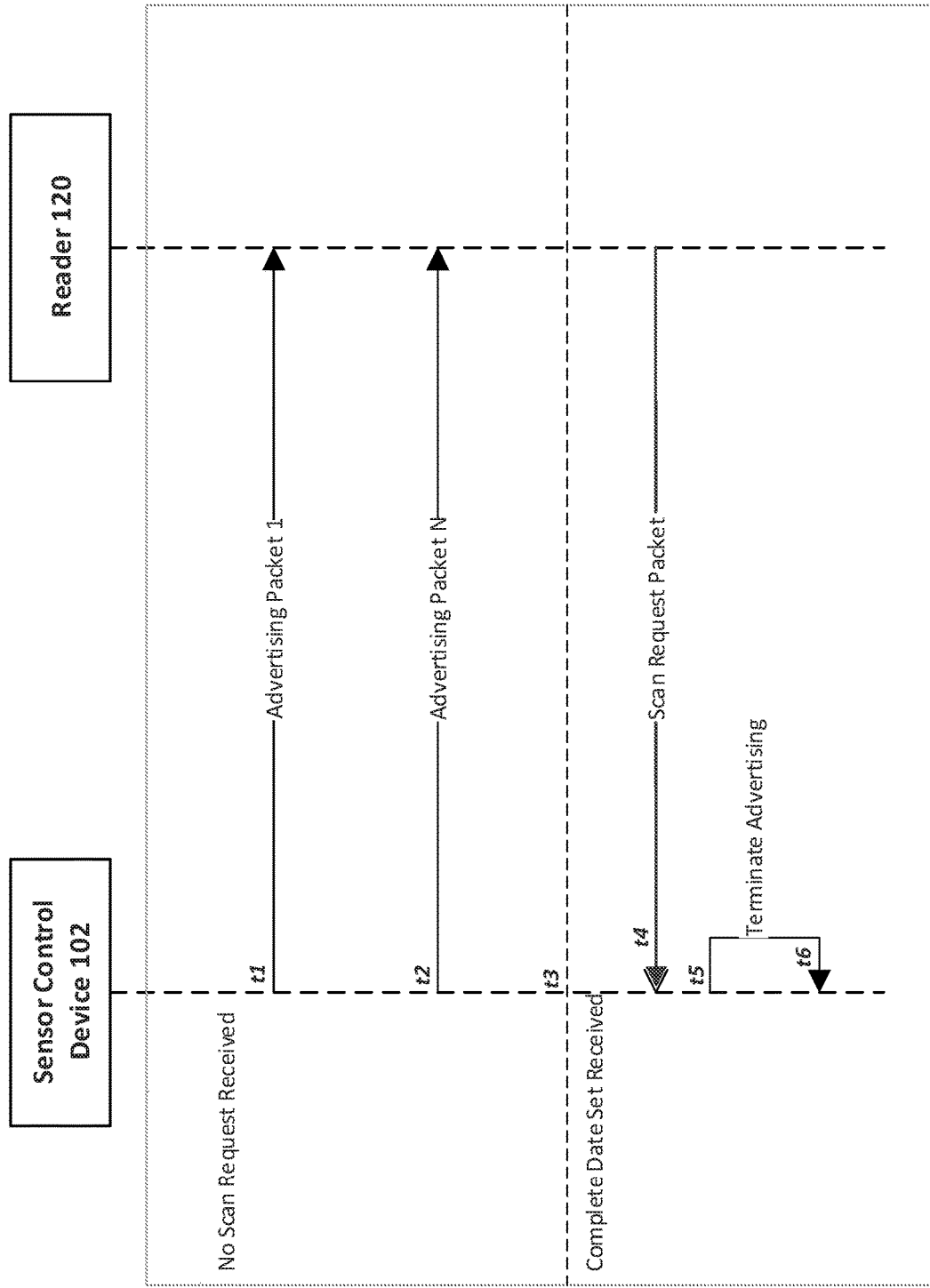
FIG. 4 is a timeline diagram depicting an example embodiment of an advertising scheme for use in an analyte monitoring system.

FIG. 4 is a timeline diagram depicting an example embodiment of an advertising scheme 400 for wireless communications between two devices in analyte monitoring system 100, which in this embodiment are sensor control device 102 and reader 120. As shown at the top of FIG. 4, according to advertising scheme 400, sensor control device 102 transmits a first advertising packet (Advertising Packet 1) in a sensor data set at time, t1, which is subsequently received by reader 120. According to one aspect of some embodiments, a sensor data set can include duplicate advertising packets which are transmitted repeatedly in a randomized order. For example, if a sensor data set includes three unique advertising packets (e.g., AP1, AP2, and AP3), each packet can be sent twice in one transmission sequence to achieve better delivery. Thus, in this example, a total of six advertising packets can be transmitted in a randomized order (e.g., AP3, AP1, AP2, AP1, AP3, AP2). In other embodiments, advertising packets in a sensor data set can be transmitted in a sequential or a non-sequential order. The sensor data set can include one, two, three, four, or more advertising packets.

According to another aspect of advertising scheme 400, to prevent advertising packets from being filtered out by the reader's operating system (as described earlier), which would result in an incomplete sensor data set, each advertising packet in a sensor data set can be associated with a different UUID, where each UUID is registered with an API of the reader's operating system, such as for example, a Bluetooth Low Energy API. Thus, with reference to the earlier example, six different UUIDs can be registered with a smart phone's BLE API. Furthermore, according to another aspect of advertising scheme 400, each advertising packet can include packet order information, so that reader 120 can reassemble the sensor data set in the correct order.

Referring back to FIG. 4, sensor control device 102 continues to transmit advertising packets (and reader 120 continues to receive advertising packets) until the last advertising packet (Advertising Packet N) in the sensor data set is transmitted at time, t2. As indicated by the horizontal dashed line, at time, t3, reader 120 has received a complete sensor data set. Subsequently, reader 120 transmits a scan request packet, also referred to as a scan request PDU, to sensor control device 102 at time, t4. Sensor control device 102 receives the scan request packet at time, t5, and, in response, stops transmitting advertising packets at time, t6 (e.g., until the next set of sensor data is ready to be sent). In this regard, in contrast to a transmit-only wireless architecture, sensor control device 102 does not blindly and repeatedly transmit advertising packets after the complete sensor data set has already been successfully received by reader 120, and unnecessary power consumption can be avoided.

Figure 5:
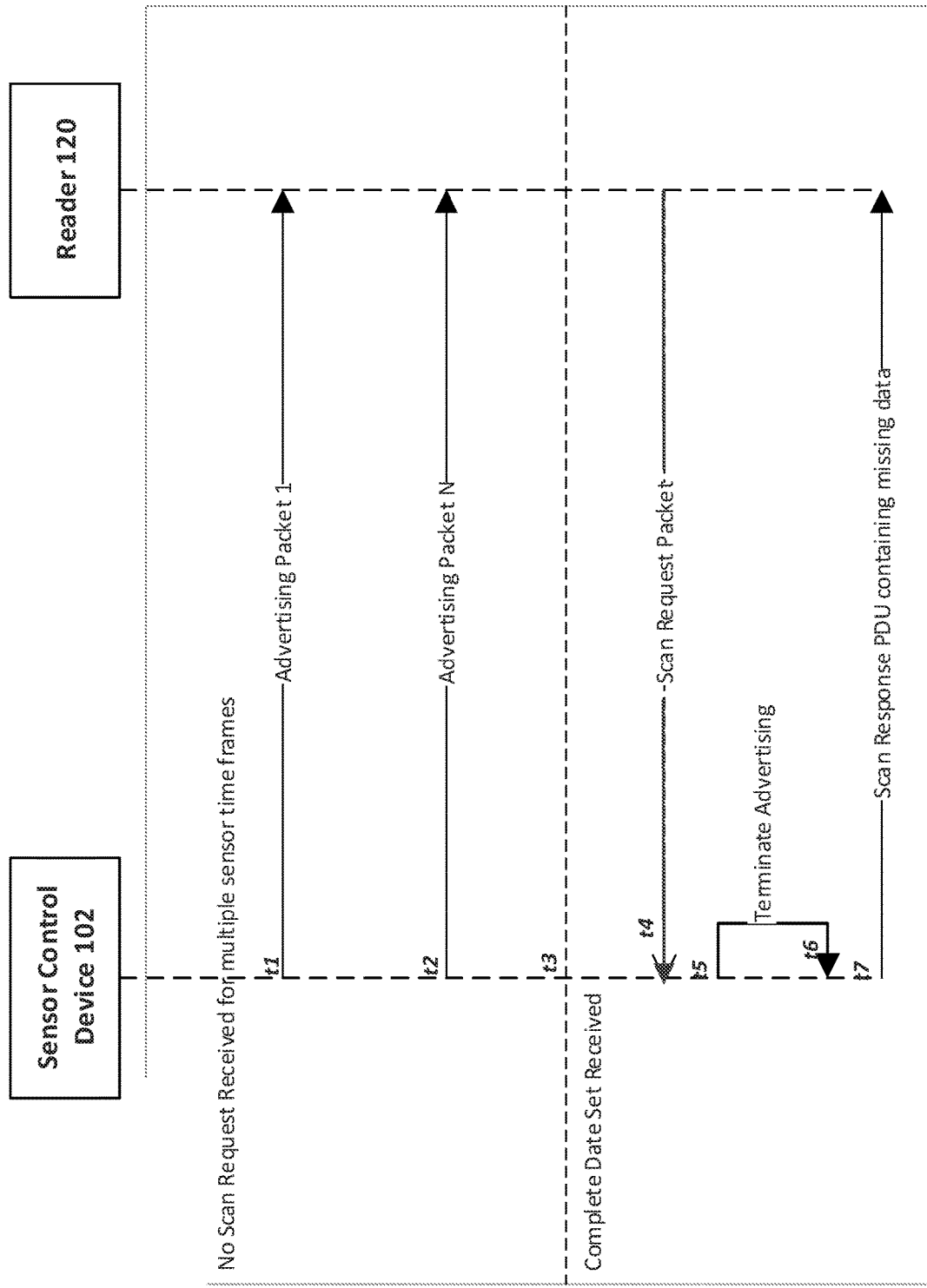
FIG. 5 is another timeline diagram depicting an example embodiment of an advertising scheme for use in an analyte monitoring system

FIG. 5 is a timeline diagram depicting another example embodiment of an advertising scheme 500 for wireless communications between devices in analyte monitoring system 100, which again are sensor control device 102 and reader 120 in this embodiment. In several aspects, advertising scheme 500 is similar to advertising scheme 500 of FIG. 4. For example, as shown at the top of FIG. 5, sensor control device 102 transmits a first advertising packet (Advertising Packet 1) in a sensor data set at time, t1, which is subsequently received by reader 120. Subsequently, sensor control device 102 continues to transmit advertising packets (and reader 120 continues to receive advertising packets) until the last advertising packet (Advertising Packet N) in the sensor data set is transmitted at time, t2. As indicated by the horizontal dashed line, at time, t3, reader 120 has received a complete sensor data set. Thereafter, reader 120 transmits a scan request to sensor control device 102 at time, t4. Sensor control device 102 receives the scan request packet at time, t5, and, in response, stops transmitting advertising packets at time, t6 (e.g., until the next set of sensor data is ready to be sent).

According to one aspect of the embodiment, advertising scheme 500 can also include a "sensor data backfilling" feature which enables sensor control device 102 to re-transmit previously unreceived sensor data to reader 120. In particular, sensor control device 102 can identify which sensor data sets have not been received by reader 120 based on not having received a corresponding scan request packet from reader 120 within a predetermined time frame. According to advertising scheme 500, if sensor control device 102 determines that it has not received a scan request packet from reader 120 for a previously transmitted sensor data set, sensor control device 102 can then transmit a scan response packet, also referred to as a scan response PDU, to reader 120 at time, t7. The scan response packet can include data indicative of the sensed analyte level from the previously transmitted sensor data set.

Figure 6:
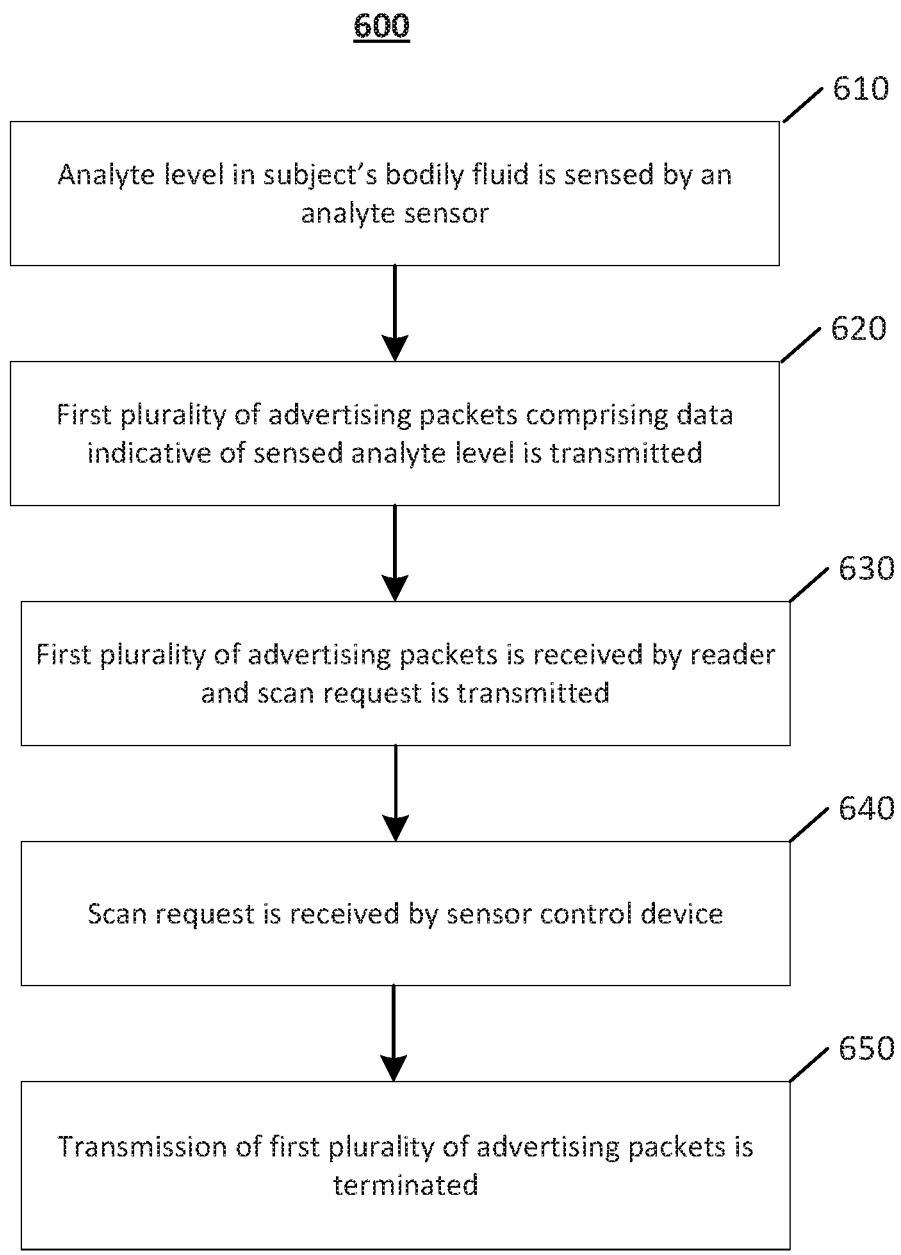
FIG. 6 is a flow chart of an example embodiment of a method for power-efficient wireless communications in an in vivo analyte monitoring system.

FIG. 6 is a flowchart diagram showing an example embodiment of method 600 for wireless communications between a sensor control device and a reader in an analyte monitoring system. At Step 610, an analyte sensor of the sensor control device senses an analyte level in a subject's bodily fluid. At Step 620, the sensor control device transmits a first plurality of advertising packets according to a wireless communications protocol such as, for example, a Bluetooth or Bluetooth Low Energy protocol. According to one aspect of method 600, the advertising packets include data indicative of the sensed analyte level. Additionally, as described earlier with respect to FIG. 4, the first plurality of advertising packets can include duplicate packets which can be repeatedly transmitted in either a sequential, non-sequential or randomized order. At Step 630, the first plurality of advertising packets is received by reader 120 in the form of, for example, a smart phone. In response to receiving the first plurality of advertising packets, reader 120 transmits a scan request to sensor control device 102. At Step 640, the scan request is received by sensor control device 102. In response to receiving the scan request, sensor control device 102 terminates the transmission of the first plurality of advertising packets at Step 650.

Figure 7:
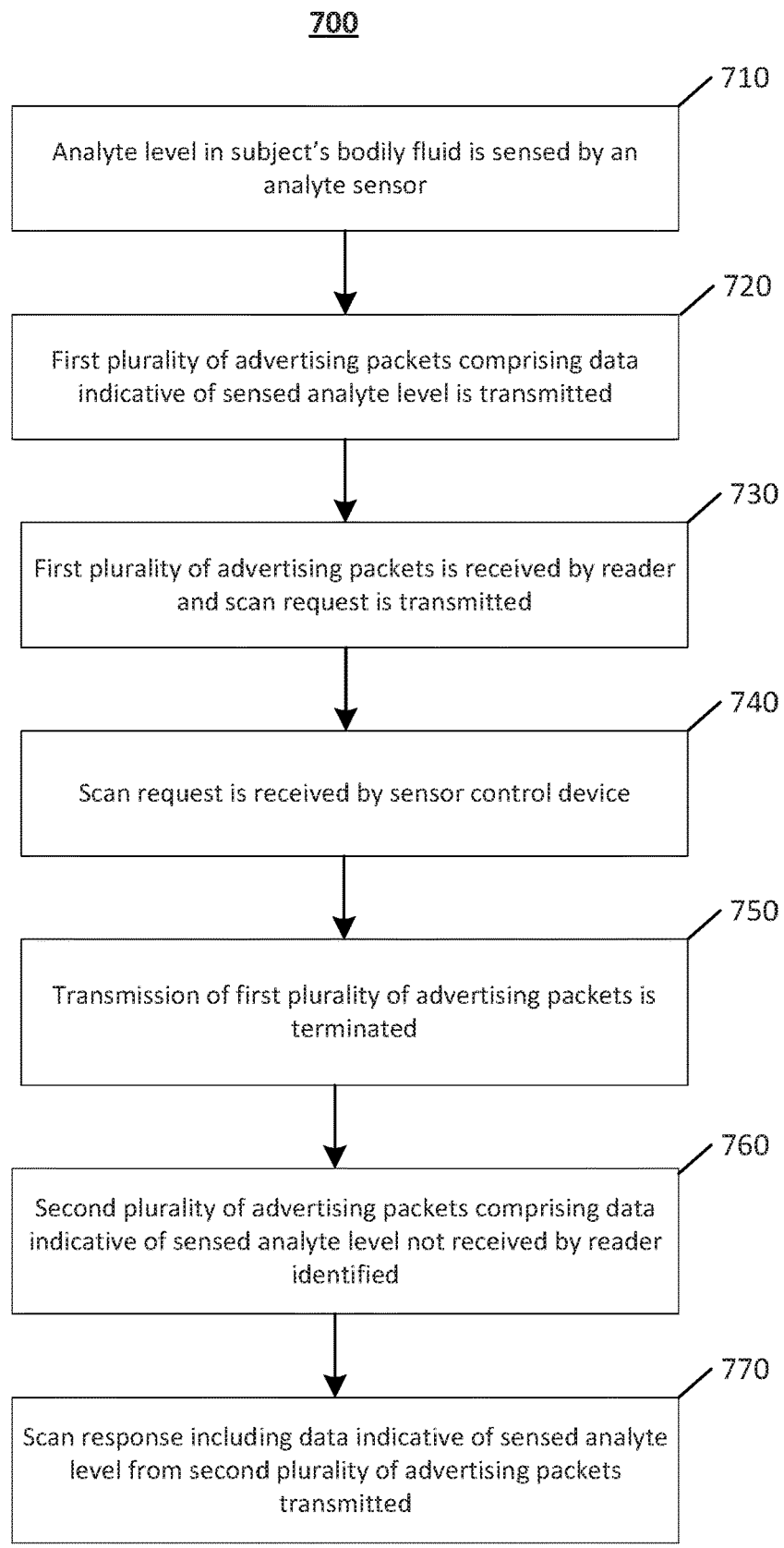
FIG. 7 is a flow chart of an example embodiment of another method for power-efficient wireless communications in an in vivo analyte monitoring system.

FIG. 7 is another flowchart diagram showing an example embodiment of method 700 for wireless communications in analyte monitoring system 100, including steps for a "sensor data backfilling" feature. Method 700 includes several of the same steps (Steps 710, 720, 730, 740, and 750) as the steps of method 600 (Steps 610, 620, 630, 640, and 650), as described with respect to FIG. 6. According to another aspect of method 700, at Step 760, sensor control device 102 can identify a second plurality of advertising packets not previously received by reader 120. In some embodiments, the second plurality of advertising packets can include advertising packets containing data indicative of a sensed analyte level which were previously transmitted by sensor control device 102, but not received by reader 120. Sensor control device 102 can identify the second plurality of advertising packets by determining that a scan request packet associated with the second plurality of advertising packets was not received from reader 120 within a predetermined time frame. In response to identifying the second plurality of advertising packets, at Step 770, sensor control device 102 can transmit a scan response packet to reader 120, where the scan response packet includes data indicative of the sensed analyte level from the second plurality of advertising packets.

Figure 8:
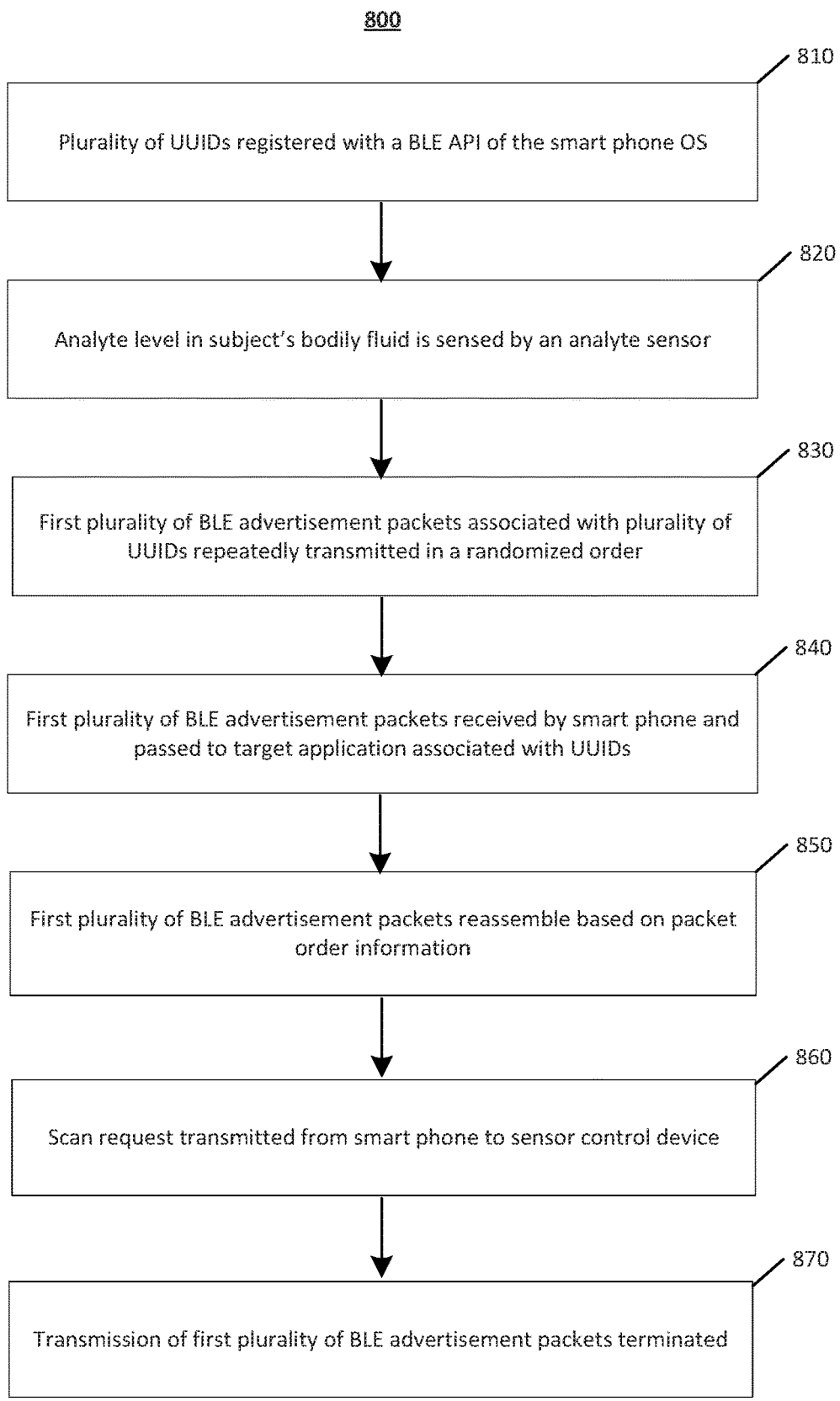
FIG. 8 is a flow chart of an example embodiment of another method for power-efficient wireless communications in an in vivo analyte monitoring system.

FIG. 8 is another flowchart diagram showing an example embodiment of method 800 for wireless communications between a sensor control device and a smart phone, where the wireless communications are performed according to a Bluetooth Low Energy protocol. At Step 810, a plurality of UUIDs is registered with a BLE API of the smart phone's operating system. At Step 820, an analyte sensor of the sensor control device senses an analyte level in a subject's bodily fluid. At Step 830, the sensor control device repeatedly transmits a first plurality of BLE advertising packets in a randomized order, where each packet is associated with a different UUID from the plurality of UUIDs registered with the BLE API of the smart phone's operating system. According to one aspect of method 800, each BLE advertising packet includes data indicative of the sensed analyte level. In some embodiments, the first plurality of BLE advertising packets can include two or more duplicate packets having the same data indicative of the sensed analyte level. At Step 840, the first plurality of BLE advertising packets is received by the smart phone and passed to a target application associated with the registered UUIDs. At Step 850, based on packet order information included with each received BLE advertising packet, the plurality of BLE advertising packets are reassembled in a sequential order. Subsequently, at Step 860, in response to receiving all of the first plurality of BLE advertising packets, the smart phone can transmit a scan request to the sensor control device. At Step 870, in response to receiving the scan request from the smart phone, the sensor control device can terminate the transmission of the first plurality of BLE advertising packets.

According to some embodiments, method 800 can also include a "sensor data backfilling" feature, as described earlier with respect to FIGS. 5 and 7. In particular, after Step 870, sensor control device can identify a second plurality of BLE advertising packets which were previously transmitted but not received by the smart phone. In some embodiments, for example, the second plurality of BLE advertising packets can be identified by the sensor control device if a scan request associated with the second plurality of BLE advertising packets has not been received by the sensor control device within a predetermined time frame. Subsequently, in response to identifying the second plurality of BLE advertising packets, the sensor control device can transmit a scan response packet containing the data indicative of the sensed analyte level associated with the second plurality of BLE advertising packets to the smart phone.

With regard to the example embodiments described respect to FIGS. 4-8, it will be understood by those of skill in the art that the data indicative of a sensed analyte level can include, but is not limited to, a glucose level, a rate of change of a glucose level, a rate of the rate of change of a glucose level (acceleration in the rate of change). Furthermore, many of the embodiments described with respect to FIGS. 4-8 make reference to an advertising scheme of a Bluetooth or a Bluetooth Low Energy protocol. However, those of skill in the art will recognize that any wireless communications protocol having a similar method of unidirectional data transmission (including but not limited to broadcasting and/or multicasting) are included within the scope of the present disclosure.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many example embodiments, a method for monitoring an analyte level in a subject is provided, the method including: sensing, by an analyte sensor, the analyte level in a bodily fluid of the subject; transmitting, by a sensor control device including sensor electronics communicatively coupled to the analyte sensor, a first plurality of advertising packets according to a wireless communications protocol, where the advertising packets include data indicative of the sensed analyte level; and terminating the transmission of the first plurality of advertising packets in response to receiving a scan request from a reader. In these embodiments, the wireless communications protocol can be a Bluetooth or a Bluetooth Low Energy protocol.

In these embodiments, the method can further include transmitting, by the reader, the scan request to the sensor control device in response to receiving the first plurality of advertising packets.

In these embodiments, the method can further include, in response to receiving the scan request from the reader, identifying, by the sensor control device, a second plurality of advertising packets not received by the reader and transmitting a scan response including data indicative of the sensed analyte level from the second plurality of advertising packets. At least a portion of the data indicative of the sensed analyte level from the second plurality of advertising packets can be different from the data indicative of the sensed analyte level from the first plurality of advertising packets.

In these embodiments, each of the first plurality of advertising packets can be associated with a different Universal Unique Identifier (UUID). The method can further include registering, by the reader, each of the UUID's with an application program interface (API) of the reader.

In these embodiments, transmitting the first plurality of advertising packets according to a wireless communications protocol can include repeatedly transmitting the first plurality of advertising packets. Transmitting the first plurality of advertising packets according to a wireless communications protocol can further include transmitting the first plurality of advertising packets in a non-sequential order. Transmitting the first plurality of advertising packets according to a wireless communications protocol can include transmitting the first plurality of advertising packets in a randomized order. Each of the first plurality of advertising packets can include packet order information. In these embodiments, the method can further include reassembling, by the reader, the data indicative of the sensed analyte level based on the packet order information.

In these embodiments, the first plurality of advertising packets can include at least one set of duplicate advertising packets. Each set of duplicate advertising packets can include two or more advertising packets containing the same data indicative of the sensed analyte level. Each of the first plurality of advertising packets can be associated with a different Universal Unique Identifier (UUID).

In these embodiments, the reader can be a smart phone. In these embodiments, the data indicative of the sensed analyte level can include a glucose level. In these embodiments, the data indicative of the sensed analyte level can include a rate of change of a glucose level.

In many embodiments, an analyte monitoring system is provided, the system including: a sensor control device including one or more processors, a memory coupled to the one or more processors, wireless communications circuitry coupled to the one or more processors, and an analyte sensor configured to sense an analyte level in a bodily fluid of a subject, where the memory stores instructions that, when executed by the one or more processors, cause the one or more processors to cause a transmission of a first plurality of advertising packets according to a wireless communications protocol, where the advertising packets include data indicative of the sensed analyte level, and terminate the transmission of the first plurality of advertising packets in response to receiving a scan request from a reader.

In these embodiments, the system can further include: a reader including one or more processors of the reader, a memory of the reader coupled to the one or more processors of the reader, and wireless communications circuitry of the reader, where the memory of the reader can store instructions that, when executed by the one or more processors of the reader, cause the one or more processors of the reader to cause a transmission of the scan request to the sensor control device in response to receiving the first plurality of advertising packets.

In these embodiments, the memory of the sensor control device can store instructions that, when executed by the one or more processors, cause the one or more processors to identify a second plurality of advertising packets not received by the reader in response to receiving the scan request, and to cause a transmission of a scan response including data indicative of the sensed analyte level from the second plurality of advertising packets.

In these embodiments, at least a portion of the data indicative of the sensed analyte level from the second plurality of advertising packets can be different from the data indicative of the sensed analyte level from the first plurality of advertising packets.

In these embodiments, each of the first plurality of advertising packets can be associated with a different Universal Unique Identifier (UUID). The memory of the reader can store instructions that, when executed by the one or more processors of the reader, cause the one or more processors of the reader to register each of the UUIDs with an application program interface (API).

In these embodiments, the memory of the sensor control device can store instructions that, when executed by the one or more processors, cause the one or more processors to cause repeated transmissions of the first plurality of advertising packets.

In these embodiments, the repeated transmissions of the first plurality of advertising packets can be in a non-sequential order or in a randomized order. Each of the first plurality of advertising packets can include packet order information. The memory of the reader can store instructions that, when executed by the one or more processors of the reader, cause the one or more processors of the reader to reassemble the data indicative of the sensed analyte level based on the packet order information.

In these embodiments, the first plurality of advertising packets can include at least one set of duplicate advertising packets. Each set of duplicate advertising packets can include two or more advertising packets including the same data indicative of the sensed analyte level. Each of the first plurality of advertising packets can be associated with a different Universal Unique Identifier (UUID).

In these embodiments, the reader can be a smart phone. The data indicative of the sensed analyte level can include a glucose level. The data indicative of the sensed analyte level can include a rate of change of a glucose level.

In these embodiments, the wireless communications protocol can be a Bluetooth or Bluetooth Low Energy protocol.

In many embodiments, a method for wirelessly transmitting data is provided, the method including: transmitting, by a first electronic device, a first plurality of advertising packets according to a wireless communications protocol, where the advertising packets include a first payload data; receiving, by a second electronic device, the first plurality of advertising packets and transmitting a scan request in response thereto; and terminating, by the first electronic device, the transmission of the first plurality of advertising packets in response to receiving the scan request from the second electronic device.

In these embodiments, the wireless communications protocol can be a Bluetooth or a Bluetooth Low Energy protocol.

In these embodiments, the method can further include: in response to receiving the scan request, identifying, by the first electronic device, a second plurality of advertising packets not received by the second electronic device; and transmitting a scan response including a second payload data associated with the second plurality of advertising packets. At least a portion of the second payload data can be different from the first payload data.

In these embodiments, each of the first plurality of advertising packets can be associated with a different Universal Unique Identifier (UUID). The method can further include registering, by the second electronic device, each of the UUIDs with an application program interface (API) of the second electronic device.

In these embodiments, transmitting the first plurality of advertising packets according to a wireless communications protocol can include repeatedly transmitting the first plurality of advertising packets. Transmitting the first plurality of advertising packets according to a wireless communications protocol can include transmitting the first plurality of advertising packets in a non-sequential order. Transmitting the first plurality of advertising packets according to a wireless communications protocol can include transmitting the first plurality of advertising packets in a randomized order. Each of the first plurality of advertising packets can include packet order information. In these embodiments, the method can further include reassembling, by the second electronic device, the first payload data based on the packet order information.

In these embodiments, the first plurality of advertising packets can include at least one set of duplicate advertising packets. Each set of duplicate advertising packets can include two or more advertising packets including the same first payload data. Each of the first plurality of advertising packets can be associated with a different Universal Unique Identifier (UUID).

In these embodiments, the second electronic device can be a smart phone. In these embodiments, the first electronic device can include a sensor and a battery.

It should also be noted that all features, elements, components, functions, and steps described with respect to any of the embodiments provided herein are intended to be freely combinable and substitutable with those from any other embodiment. For example, any and all of the features, elements, components, functions, and steps described with respect to FIGS. 1A-1F and FIGS. 4-8 can be combined or interchanged. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method for wireless communications between a first electronic device and a second electronic device, the method comprising:
   repeatedly transmitting, by the first electronic device, a first plurality of advertising packets according to a wireless communications protocol, wherein the first plurality of advertising packets comprises a first set of payload data;
   receiving, by the first electronic device, a scan request from the second electronic device;
   terminating, by the first electronic device, a transmission of the first plurality of advertising packets in response to the received scan request;
   identifying, by the first electronic device, a second plurality of advertising packets comprising a second set of payload data that was not received by the second electronic device; and
   transmitting, by the first electronic device, a scan response according to the wireless communications protocol, wherein the scan response includes the second set of payload data.

2. The method of claim 1, further comprising transmitting, by the second electronic device, the scan request in response to receiving the first plurality of advertising packets.

3. The method of claim 1,
   wherein identifying the second plurality of advertising packets that was not received by the second electronic device comprises identifying, by the first electronic device, a missing scan request from a plurality of received scan requests.

4. The method of claim 1, wherein the wireless communication protocol comprises a Bluetooth or a Bluetooth Low Energy protocol.

5. The method of claim 1, wherein the first electronic device is a sensor control device.

6. The method of claim 1, wherein the second electronic device is a reader device.

7. The method of claim 1, wherein the second electronic device is a smart phone.

8. The method of claim 1, wherein the first set of payload data comprises one or more of a sensed analyte level, a sensed temperature measurement, a sensed pressure measurement, a sensed force measurement, a sensed acceleration measurement, and a sensed physiological measurement.

9. The method of claim 1, wherein the first set of payload data comprises a first set of data indicative of a sensed analyte level.

10. The method of claim 9, wherein the second set of payload data comprises a second set of data indicative of a sensed analyte level.

11. The method of claim 10, wherein at least a portion of the first set of data indicative of the sensed analyte level is different from the second set of data indicative of the sensed analyte level.

12. The method of claim 1, wherein transmitting the first plurality of advertising packets according to the wireless communications protocol further comprises transmitting the first plurality of advertising packets in a non-sequential order.

13. The method of claim 1, wherein transmitting the first plurality of advertising packets according to the wireless communications protocol further comprises transmitting the first plurality of advertising packets in a randomized order.

14. The method of claim 13, wherein each advertising packet of the first plurality of advertising packets includes packet order information.

15. The method of claim 14, further comprising reassembling, by the second electronic device, the first set of payload data based on the packet order information.

16. The method of claim 1, wherein each advertising packet of the first plurality of advertising packets is associated with a different Universal Unique Identifier (UUID).

17. The method of claim 16, further comprising, registering, by the second electronic device, each of the UUIDs with an application program interface (API) of the second electronic device.

18. The method of claim 1, wherein the first plurality of advertising packets comprises at least one set of duplicate advertising packets.

19. The method of claim 3, further comprising:
tracking, by the first electronic device, the plurality of received scan requests received from the second electronic device; and
associating, by the first electronic device, each of the plurality of received scan requests with a corresponding plurality of advertising packets received by the second electronic device.

20. The method of claim 19, wherein tracking the plurality of received scan requests further comprises tracking the plurality of received scan requests received within a predetermined time frame.

* * * * *